US00PP25516P2

(12) United States Plant Patent
Hanna et al.

(10) Patent No.: US PP25,516 P2
(45) Date of Patent: May 5, 2015

(54) GRASS 'TIFT 118'

(50) Latin Name: ***Pennisetum purpureum*×[*Pennisetum glaucum*×(*Pennisetum purpureum*×*Pennisetum squamulatum*)]**
Varietal Denomination: Tift 118

(71) Applicant: University of Georgia Research Foundation, Inc., Athens, GA (US)

(72) Inventors: Wayne W. Hanna, Chula, GA (US); S. Kristine Braman, Griffin, GA (US); Brian M. Schwartz, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 155 days.

(21) Appl. No.: 13/986,881

(22) Filed: Jun. 13, 2013

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para
(74) *Attorney, Agent, or Firm* — Klarquist Sparkman, LLP

(57) ABSTRACT

The new variety *Pennisetum* 'Tift 118' is provided. The new and distinct variety has high ornamental value, cold tolerance for short periods of time, and disease resistance. The asexually reproduced variety is reliably propagated vegetatively.

1 Drawing Sheet

Latin name of the genus and species of the plant claimed: 'Tift 118' is a tri-specific ornamental *Pennisetum* hybrid of the genus and species *Pennisetum purpureum*×[*Pennisetum glaucum*×(*Pennisetum purpureum*×*Pennisetum squamulatum*)].

Variety denomination: The new *Pennisetum* claimed is of the variety denominated 'Tift 118'.

BACKGROUND OF THE INVENTION

The present invention relates to a new and distinct cultivar of *Pennisetum* herein referred to as 'Tift 118'.

The new *Pennisetum* 'Tift 118' is a product of a planned breeding program conducted by the Inventors in Tifton, Ga. The objective of the *Pennisetum* breeding program is to create new plant cultivars with improved commercial qualities. This cultivar is commercially important for its superior ornamental value. These and other qualities are enumerated herein.

Pedigree and history: In 2003, red tetraploid (2n=4x=28) pearl millet (unpatented *Pennisetum glaucum*; designated '04-94') was crossed with SC 1125-2 [a Merkeron napiergrass (unpatented *Pennisetum purpureum;* 2n=4x=28) that had been crossed with PS 262 (unpatented *Pennisetum squamulatum;* 2n=8x=56)]. One vigorous plant, from the 04-94/SC 1125-2 cross, designated '04-26-1', was selected in 2004. In 2004, 'Princess' napiergrass (U.S. Plant Pat. No. 17,728; 2n=4x=28, female parent) was pollinated with '04-26-1' (unpatented; male parent). The new variety 'Tift 118' was the 118th plant selected in 2006 from the 2004 cross. The new variety 'Tift 118' has been tested since 2007.

Asexual reproduction of the new *Pennisetum* 'Tift 118' by vegetative propagation (single stem propagules) in a controlled environment in Tifton, Blairsville, and Griffin, Ga. since 2007, has shown that the unique features of this new *Pennisetum* hybrid are stable and reproduced true to type in successive generations.

SUMMARY OF THE INVENTION

The following traits have been repeatedly observed and represent the characteristics of a new variety *Pennisetum*, 'Tift 118'. The new variety 'Tift 118' has not been observed under all possible environmental conditions. The phenotype may vary somewhat with variations in, for example, temperature, day-length, light intensity, soil types, and water and fertility levels without, however, any variance in genotype.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following traits have been repeatedly observed in Tifton, Blairsville, and Griffin, Ga., and are determined to be the unique characteristics of the new variety 'Tift 118':

1. 'Tift 118' reaches a height of about 1.7 meters, and a spread of about 1.8 meters.
2. 'Tift 118' exhibits a vigorous growth habit.
3. 'Tift 118' is pollen and seed sterile.

The new variety *Pennisetum* 'Tift 118' can be compared to its parents, 'Princess' and '04-26-01', and its sister hybrid, 'Tift 8' (U.S. Plant Pat. No. 22,254).

Plants of the new *Pennisetum* differ from its female parent 'Princess' in the following characteristics:

1. The new variety 'Tift 118' is taller than 'Princess'.
2. The leaf length and width of the new variety 'Tift 118' is larger that that of 'Princess'.

Plants of the new *Pennisetum* differ from its male parent '04-26-1' in the following characteristics:

1. The new variety 'Tift 118' is slightly different from '04-26-1' in adaxial leaf color. The new variety 'Tift 118' is mottled Greyed-purple/green RHS 187B/137B, whereas '04-26-1' is about mottled Greyed-purple/green RHS 183B/138A.
2. The new variety 'Tift 118' has a different midrib color. The midrib color of the new variety 'Tift 118' is about Greyed-purple RHS 187A, while the midrib color of '04-26-1' is about Red-purple RHS 61C.

Plants of the new *Pennisetum* differ from its sister hybrid 'Tift 8' in the following characteristics:

1. The new variety 'Tift 118' is significantly taller than 'Tift 8'.

The following observations, measurements, and values describe plants grown in Tifton and Blairsville, Ga. In Tables 1-5, the least significant difference (LSD) is set at P≤0.05 probability level. Growth days were included in ratings. Plants were spaced at 2 meter centers. All data are from plants established as single stem propagules in mid-May and rated in September through October, except the data from 2010 and 2011, in which the plants had been overwintered at Tifton, Ga.

The new variety 'Tift 118' was taller than 'Tift 8' in all of the six tests and was significantly taller than 'Tift 8' in three of six tests in Tifton and Blairsville, Ga. (Table 1). The canopy diameter for 'Tift 118' was wider than 'Tift 8' in all of the six tests and significantly wider than 'Tift 8' in four of five tests in Georgia (Table 2). 'Tift 118' has an attractive reddish/purple color and was equal in color to 'Tift 8' at Blairsville, but showed significantly less, though still acceptable, color in three tests at Tifton (Table 3). The new variety 'Tift 118', similar to 'Tift 8', is not disease-susceptible to *Helminthosporium* leaf spot, whereas 'Princess' is susceptible to this disease (Table 4). Leaves of 'Tift 118' are significantly longer, wider, and have more leaf area than leaves of 'Tift 8' (Table 5). Culm-leaf angle was equal for 'Tift 118' and 'Tift 8' in the test set forth in Table 5.

TABLE 1

Plant heights (cm) of two ornamental *Pennisetum* grasses planted at two locations in Georgia.

| | Tifton | | | Blairsville | |
|---|---|---|---|---|---|
| | 2009 | 2010 | 2011 | 2011 | 2012 |
| Growth days | 153 d | 150 d | 183 d | 160 d | 158 d |
| 'Tift 118' | 120 | 129 | 135 | 173 | 164 |
| 'Tift 8' | 115 | 116 | 95 | 136 | 128 |
| LSD | NS | NS | 14 | 25 | 14 |

In Table 1, plant heights were measured from ground level to top of plant canopy. All height measurements are in cm. At Tifton, Ga., 'Tift 118' and 'Tift 8' were planted on May 9, 2009, May 9, 2010, and May 12, 2011, with measurements taken on Oct. 12, 2009, Sep. 29, 2010, and Oct. 18, 2011. At Blairsville, Ga., 'Tift 118' and 'Tift 8' were planted on May 1, 2011 and Apr. 4, 2012, with measurements made on Oct. 10, 2011 and Sep. 19, 2012, respectively.

TABLE 2

Canopy diameter(cm) of individual plant of two ornamental *Pennisetum* grasses planted at two locations in Georgia. Plants were spaced on two meter centers.

| | Tifton | | | Blairsville | |
|---|---|---|---|---|---|
| | 2009 | 2010 | 2011 | 2011 | 2012 |
| Growth days | 153 d | 150 d | 183 d | 160 d | 158 d |
| 'Tift 118' | 156 | 155 | 154 | 177 | 173 |
| 'Tift 8' | 155 | 130 | 120 | 159 | 151 |
| LSD | NS | 13 | 10 | 17 | 12 |

Plant canopy measurements, as shown in Table 2, represent the average diameters measured at the estimated widest and narrowest portions of a single plant canopy. Measurements are in cm. At Tifton, Ga., 'Tift 118' and 'Tift 8' were planted on May 9, 2009, May 9, 2010, and May 12, 2011, with measurements taken on Oct. 12, 2009, Sep. 29, 2010, and Oct. 18, 2011. At Blairsville, Ga., 'Tift 118' and 'Tift 8' were planted on May 1, 2011 and Apr. 4, 2012, with measurements made on Oct. 10, 2011 and Sep. 19, 2012.

TABLE 3

Color ratings on individual plants of two ornamental *Pennisetum* grasses planted at two locations in Georgia. Plants were spaced on two meter centers.

| | Tifton | | | Blairsville | |
|---|---|---|---|---|---|
| | 2009 | 2010 | 2011 | 2011 | 2012 |
| Growth days | 153 d | 150 d | 183 d | 160 d | 158 d |
| 'Tift 118' | 7.0 | 7.0 | 7.0 | 8.0 | 8.0 |
| 'Tift 8' | 9.0 | 8.1 | 8.1 | 8.0 | 8.0 |
| LSD | 0.2 | 0.9 | 0.6 | 0.6 | NS |

Color ratings are measured on a scale of 1 to 9, where 1 represents green and 9 represents dark purple/red. At Tifton, Ga., 'Tift 118' and 'Tift 8' were planted May 9, 2009, May 9, 2010, and May 12, 2011, with measurements taken on Oct. 12, 2009, Sep. 29, 2010, and Oct. 18, 2011. At Blairsville, Ga., 'Tift 118' and 'Tift 8' were planted on May 1, 2011 and Apr. 4, 2012, with measurements taken on Oct. 10, 2011 and Sep. 19, 2012.

TABLE 4

*Helminthosporium* leaf spot ratings on two ornamental *Pennisetum* grasses planted at two locations in Georgia.

| | Tifton | | | Blairsville | |
|---|---|---|---|---|---|
| | 2009 | 2010 | 2011 | 2011 | 2012 |
| Growth days | 153 d | 150 d | 183 d | 160 d | 158 d |
| 'Tift 118' | 1.0 | 1.0 | 1.0 | 1.0 | 1.0 |
| 'Tift 8' | 1.0 | 1.0 | 1.0 | 1.0 | 1.0 |
| 'Princess' | 5.2 | 6.6 | 8.0 | 5.0 | 7.6 |
| LSD | 0.4 | 0.1 | 0.0 | 0.2 | 0.2 |

Disease ratings in Table 9 are defined as follows: 1=No disease, 2=1-20%, 3=21-30%, 4=31-40%, 5=41-50%, 6=51-60%, 7=61-70%, 8=71-80%, 9=>80% leaves infected. Symptoms occur in the field during late August and September. At Tifton, Ga., 'Tift 118' and 'Tift 8' were planted on May 9, 2009, May 9, 2010, and May 12, 2011, with measurements taken on Oct. 12, 2009, Sep. 29, 2010, and Oct. 18, 2011. At Blairsville, Ga., 'Tift 118' and 'Tift 8' were planted on May 1, 2011 and Apr. 4, 2012, with measurements taken on Oct. 10, 2011 and Sep. 19, 2012.

TABLE 5

Leaf characteristics of individual plants of two ornamental *Pennisetum* grasses planted at Tifton, Georgia in 2009. Plants were spaced on two meter centers.

| Entry | Leaf Length(cm) | Leaf Width(mm) | Leaf Area($cm^2$) | Leaf Angle culm:Leaf |
|---|---|---|---|---|
| 'Tift 118' | 91 | 46 | 305 | 81 |
| 'Tift 8' | 82 | 42 | 245 | 81 |
| LSD | 6 | 4 | 33 | NS |

The leaf length was measured in cm from the leaf collar to the leaf tip of the latest fully extended leaf. The leaf width was measured in mm in the center of the latest fully extended leaf.

The leaf area was measured in $cm^2$ using a LiCor area meter using the mean of three leaves per replication. The measured leaf angle was the angle observed between the adaxial leaf angle surface and the culm at the leaf collar on the last fully extended leaf and was measured in degrees. At Tifton, Ga., 'Tift 118' was planted on May 9, 2009, with measurements taken on Sep. 12, 2009.

TABLE 6

Summary of morphological characteristics of two *Pennisetum* grasses.

| Trait | 'Tift 8' | 'Tift 118' |
|---|---|---|
| Mature plant height | 95-136 cm | 129-173 cm |
| Diameter of plant canopy | 120-159 cm | 154-177 cm |
| Leaf width | 42 mm | 46 mm |
| Leaf length | 82 cm | 91 cm |
| Leaf Area-$cm^2$ | 245 | 305 |
| Leaf Angle (culm:Leaf) | 9 degrees | 9 degrees |
| Adaxial leaf surface trichomes | Few 1 mm along either side of midrib | Dense 1.0 mm (4 mm along midrib) for 10 cm from collar |
| Abaxial leaf surface trichomes | None | None |
| Leaf blade margin trichome length | Slight remnant less than 0.1 mm | Continuous, less than 0.1 mm |
| Leaf collar trichome length | Dense 2 mm | Dense, 5 mm |
| Leaf blade edge at collar Trichome | Moderate 5 mm long for 6 cm from collar | 5 mm long for 5 cm from collar |
| Sheath trichomes | None | Dense 0.5 mm |
| Adaxial leaf color | Greyed-purple 186C | Mottled Greyed-purple/green 187B137B |
| Abaxial leaf color | Greyed-purple 186C | Greyed-purple 187B |
| Midrib color | Greyed-purple 187E | Greyed-purple 187A |
| Inflorescences on Dec. 21, 2009 | Yes | Yes |
| *Helminthosporium* leaf spot on mature plants | None | None |

In summary, 'Tift 118' is similar to 'Tift 8' in disease resistance and is either equal in color or has significantly less, but still acceptable, color. 'Tift 118' tends to be taller, has longer, wider leaves with more leaf area per leaf than 'Tift 8'.

BRIEF DESCRIPTION OF THE FIGURES

The accompanying colored photographs illustrate the overall appearance and distinct characteristics of the new variety of *Pennisetum* 'Tift 118'. The colors in the photographs are as close as possible with the photographic and printing technology utilized.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

FIG. 1 is a photograph of the new variety *Pennisetum* 'Tift 118'.

BOTANICAL DESCRIPTION

The new variety 'Tift 118' is a perennial at Tifton, Ga. (USDA Zone 8a). The new variety 'Tift 118' survived −6° C. for one night and 21 nights below 0° C. in the field during the 2009/2010 winter at Tifton. It also survived the winter temperatures (−7° C. for one night and 24 nights below 0° C. in the field during 2010/2011) in Tifton. It has not survived the winter temperatures in the mountains of Blairsville, Ga. (USDA Zone 6b). Because of its vigor, it can effectively be used as an annual in locations where it will not survive freezing temperatures in the winter.

All data are from plants established as single stem propagules in mid-May, and rated in September through October, except the 2010 and 2011 data are from plants that over-wintered at Tifton. Plants were spaced at 2 meter centers.

Plant:

*Mature plant height*.—Approximately 129-173 cm.

*Diameter of plant canopy*.—Approximately 154-177 cm.

Leaf:

*Leaf width*.—Approximately 46 mm.

*Leaf length*.—Approximately 91 cm.

*Adaxial leaf surface trichomes*.—Dense 1.0 mm (4 mm along midrib) for 10 cm from collar.

*Abaxial leaf surface trichomes*.—None.

*Leaf blade margin trichome length*.—Continuous, less than 0.1 mm.

*Leaf collar trichome length*.—Dense, 5 mm.

*Leaf blade edge at collar trichome*.—5 mm long for 5 cm from collar.

*Sheath trichomes*.—Dense 0.5 mm.

*Adaxial leaf color*.—Mix of Greyed-purple 187B and Green 137B.

*Abaxial leaf color*.—About Greyed-purple RHS 187B.

*Midrib color*.—About Greyed-purple RHS 187A.

*Helminthosporium leaf spot on mature plants*.—None.

*Inflorescence*.—Yes.

What is claimed is:

1. A new and distinct variety of the *Pennisetum* plant named 'Tift 118', substantially as illustrated and described herein.

* * * * *

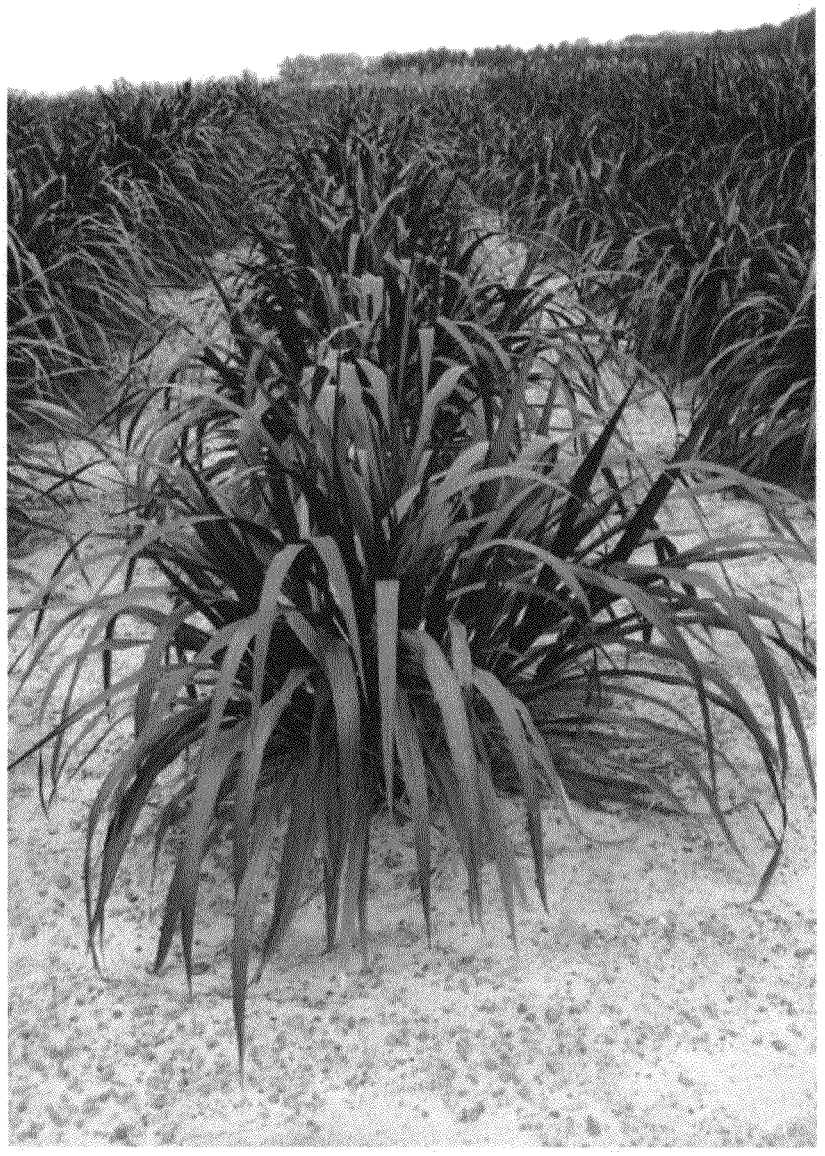

UNITED STATES PATENT AND TRADEMARK OFFICE

CERTIFICATE OF CORRECTION

PATENT NO. : PP25,516 P2
APPLICATION NO. : 13/986881
DATED : May 5, 2015
INVENTOR(S) : Hanna et al.

It is certified that error appears in the above-identified patent and that said Letters Patent is hereby corrected as shown below:

On the Title Page:

Item (50) Latin Name: "*Pennisetum purpureum x [Pennisetum glaucum x (Pennisetum purpureum x Pennisetum squamulatum)]*" should read -- *Pennisetum* hybrid --

Signed and Sealed this
Eighth Day of March, 2016

Michelle K. Lee

Michelle K. Lee
*Director of the United States Patent and Trademark Office*